US012697297B2

(12) United States Patent
Nakamura et al.

(10) Patent No.: US 12,697,297 B2
(45) Date of Patent: Aug. 4, 2026

(54) OILY SOLID COSMETIC

(71) Applicant: L V M H RECHERCHE, Saint-Jean de Brave (FR)

(72) Inventors: Kyosuke Nakamura, Tokyo (JP); Koichi Hata, Tokyo (JP)

(73) Assignee: L V M H RECHERCHE, Saint-Jean de Brave (FR)

( * ) Notice: Subject to any disclaimer, the term of this patent is extended or adjusted under 35 U.S.C. 154(b) by 199 days.

(21) Appl. No.: 17/787,256

(22) PCT Filed: Dec. 18, 2020

(86) PCT No.: PCT/EP2020/087021
§ 371 (c)(1),
(2) Date: Jun. 17, 2022

(87) PCT Pub. No.: WO2021/123164
PCT Pub. Date: Jun. 24, 2021

(65) Prior Publication Data
US 2023/0054819 A1 Feb. 23, 2023

(30) Foreign Application Priority Data
Dec. 20, 2019 (WO) .................. PCT/IB2019/001421

(51) Int. Cl.
| | |
|---|---|
| *A61K 8/92* | (2006.01) |
| *A61K 8/02* | (2006.01) |
| *A61K 8/37* | (2006.01) |
| *A61K 8/39* | (2006.01) |
| *A61Q 1/04* | (2006.01) |

(52) U.S. Cl.
CPC ............ *A61K 8/922* (2013.01); *A61K 8/0229* (2013.01); *A61K 8/37* (2013.01); *A61K 8/39* (2013.01); *A61Q 1/04* (2013.01); *A61K 2800/42* (2013.01)

(58) Field of Classification Search
None
See application file for complete search history.

(56) References Cited

U.S. PATENT DOCUMENTS

| | | | | |
|---|---|---|---|---|
| 5,849,318 A | * | 12/1998 | Imai .................... | A61K 8/8152 |
| | | | | 514/844 |
| 11,752,076 B2 | | 9/2023 | Kaneko et al. | |
| 2009/0280077 A1 | | 11/2009 | Yoshida et al. | |
| 2014/0105845 A1 | * | 4/2014 | Bui .................... | A61K 8/0241 |
| | | | | 424/70.7 |
| 2019/0307672 A1 | * | 10/2019 | Shibata ................ | A61K 8/0216 |
| 2019/0388306 A1 | * | 12/2019 | Ravni .................. | A61K 8/0229 |
| 2021/0145707 A1 | | 5/2021 | Ibe et al. | |

FOREIGN PATENT DOCUMENTS

| | | | |
|---|---|---|---|
| CN | 107281031 | * | 10/2017 |
| CN | 107595679 A | | 1/2018 |
| JP | 10-512299 A | | 11/1998 |
| JP | 2006-342141 A | | 12/2006 |
| JP | 4864414 B2 | | 2/2012 |
| JP | 2019-199411 A | | 11/2019 |
| WO | WO 97/16157 A1 | | 5/1997 |
| WO | WO 2009/139092 A1 | | 11/2009 |
| WO | WO-2018/123824 A1 | | 7/2018 |
| WO | WO 2018/212223 A1 | | 11/2018 |
| WO | WO 2019/188842 A1 | | 10/2019 |

OTHER PUBLICATIONS

Jia Qui Refine Chemical, Be Unique Lipstick 2017.*
Rigano "Formulating Lip gloss".2015.*
Jia Qi Refine Chemical, "Be Unique Lipstick" GNPD, Mintel, Aug. 24, 2017.
International Search Report and Written Opinion for Corresponding International Application No. PCT/EP2020/087021, mailing date Mar. 29, 2021.
International Search Report and Written Opinion for Corresponding International Application No. PCT/IB2019/001421, mailing date Jul. 10, 2020.
Cativa Natureza, "Lipstick," Mintel, Record ID: 5353011, Jan. 9, 2018, 4 pages total.
European Communication pursuant to Article 94(3) EPC for European Application No. 20 838 002.2, dated Aug. 29, 2024.
Maybelline, "Python Metallic Lip Kit," Mintel, Record ID: 5412855, Jan. 31, 2018, 4 pages total.
Japanese Office Action for Japanese Application No. 2022-537103, dated Jan. 21, 2025, with English translation.
Tamura et al., "2. Waxes," New Cosmetics Handbook, Oct. 30, 2006, p. 21 (9 pages total), with partial English translation.
Japanese Office Action for Japanese Application No. 2022-537103, dated Sep. 9, 2025, with English translation.

* cited by examiner

*Primary Examiner* — Danah Al-Awadi
(74) *Attorney, Agent, or Firm* — Birch, Stewart, Kolasch & Birch, LLP

(57) ABSTRACT

The present invention relates to an oily solid cosmetic comprising (A) candelilla wax, (B) a plant-based and/or animal based wax with a melting point of 70° C. or higher, (C) a monoester of a monovalent straight-chain saturated fatty acid and a monohydric straight-chain saturated aliphatic alcohol, having a total of 40 to 48 carbon atoms, and (D) at least one selected from the group consisting of (polyglyceryl-2 isostearate/dimer dilinoleate) copolymer, hydrogenated castor oil dimer dilinoleate, hydrogenated castor oil isostearate, phytosteryl/octyldodecyl lauroyl glutamate, octyldodecyl stearoyl stearate, polyglyceryl-10 isostearate, polyglyceryl-10 diisostearate, polyglyceryl-10 decaisostearate, and polybutene, or 8 mass % or less of dimer dilinoleyl diisostearate and/or dimer dilinoleyl dimer dilinoleate with respect to the total amount of the oily solid cosmetic.

8 Claims, No Drawings

OILY SOLID COSMETIC

CROSS REFERENCE TO RELATED APPLICATIONS

This Application is a U.S. National Stage of International Patent Application No. PCT/EP2020/087021 filed Dec. 18, 2020, which claims benefit priority of International Patent Application No. PCT/IB2019/001421 filed on Dec. 20, 2019, the respective disclosures of which are each incorporated herein by reference in their entireties.

TECHNICAL FIELD

The present invention relates to an oily solid cosmetic, in particular for lips.

BACKGROUND OF THE INVENTION

Many naturally-derived cosmetics have been emerging in the markets in recent years, from the viewpoint of safety and beauty. In the midst of this market situation, consumer demand for naturally-derived oily solid cosmetics has also been increasing. WO2018/123824, for example, discloses a solid wax composition comprising candelilla wax, behenyl behenate and liquid oil. JP 2006-342141A discloses an oily solid cosmetic comprising candelilla wax organic pigment and liquid oil.

Technical Problem

For conventional oily solid cosmetics such as lipstick, hydrocarbon wax with a high melting point, such as polyethylene wax, has been considered a necessary component for maintaining stability of the product. A combination of hydrocarbon wax and a polar oil provides the oily solid cosmetic with excellent stability at high temperatures.

However, in addition to high-temperature stability, oily solid cosmetics are required to have excellent texture, including smooth gliding and a melting sensation when they are applied onto skin or lips. When an oily solid cosmetic is contacted while being slid over the skin to apply it onto the skin or lips, it sometimes sticks to the skin or lips or glides in an insufficiently smooth manner, making it impossible to properly adhere the cosmetic to the skin or lips. In addition, if an oily solid cosmetic that comprises a colorant, such as lipstick, is inferior in terms of the smooth gliding or melting sensation, the cosmetic may not adhere properly onto the skin, resulting in poor coloring.

In order to improve the melting sensation and smooth gliding, a wax with a low melting point or a paste-like oil (semi-solid wax) may be used in an oily solid cosmetic. However, it is difficult to improve the texture without loss of adequate high-temperature stability. When a naturally-derived wax is used, in particular, it is difficult to achieve both a melting sensation, smooth gliding and high-temperature stability, compared to a conventional oily solid cosmetic containing primarily hydrocarbon wax.

Oily solid cosmetics are also required to have high durability. In the case of an oily solid cosmetic in the form of a stick, for example, if its durability is poor the cosmetic can potentially break when it is let out from the container, or it may not be firmly molded during production. Moreover, with a solid cosmetic filled into a shallow container such as a compact container, for example, if its durability is poor it may undergo splitting or cracking, or significantly larger amounts than necessary may adhere to the brush or sponge during use.

So it is an object of the present invention to provide an oily solid cosmetic comprising a naturally-derived wax, in particular a plant-based and/or animal-based wax, which is excellent in terms of both melting sensation, smooth gliding, and also especially high-temperature stability and durability. By 'naturally-derived wax' according to the invention, it means plant-derived and/or animal-derived wax, also named in the rest of the description as 'planted-based and/or animal-based wax'. Here 'naturally-derived wax' does not include petroleum derived wax. The inventors demonstrate in illustrative and comparative examples further in the description that the combination of (A) to (D) compounds according to the invention answers the technical problem to have both melting sensation, smooth gliding, and also especially high-temperature stability and durability, in comparison to prior compositions missing one or two of the compounds of the combination.

SUMMARY OF THE INVENTION

One aspect of the present invention relates to an oily solid cosmetic comprising (A) candelilla wax, (B) a plant-based and/or animal-based wax with a melting point of 70° C. or higher, (C) a monoester of a monovalent straight-chain saturated fatty acid and a monohydric straight-chain saturated aliphatic alcohol, having a total of 40 to 48 carbon atoms, and (D) at least one selected from the group consisting of (polyglyceryl-2 isostearate/dimer dilinoleate) copolymer, hydrogenated castor oil dimer dilinoleate, hydrogenated castor oil isostearate, phytosteryl/octyldodecyl lauroyl glutamate, octyldodecyl stearoyl stearate, polyglyceryl-10 isostearate, polyglyceryl-10 diisostearate, polyglyceryl-10 decaisostearate, and polybutene.

Another aspect of the present invention relates to an oily solid cosmetic comprising: (A) candelilla wax, (B) a plant-based and/or animal-based wax with a melting point of 70° C. or higher, (C) a monoester of a monovalent straight-chain saturated fatty acid and a monohydric straight-chain saturated aliphatic alcohol, having a total of 40 to 48 carbon atoms, and (D) 8 mass % or less of dimer dilinoleyl diisostearate and/or dimer dilinoleyl dimer dilinoleate with respect to the total amount of the oily solid cosmetic.

The plant-based wax is preferably at least one selected from the group consisting of rice bran wax, carnauba wax and sunflower seed wax.

The monoester is preferably at least one selected from the group consisting of behenyl stearate, arachidyl eicosanoate, henicosyl eicosanoate, behenyl eicosanoate, stearyl behenate, nonadecanyl behenate, arachidyl behenate, henicosyl behenate and behenyl behenate.

The cosmetic preferably further comprises a liquid oil having at least one hydroxyl group, in addition to component (D).

The cosmetic may be a lip rouge, a cheek rouge, a lip balm, a lip liner, a foundation, a concealer, a face color, an eyeliner, or an eye shadow.

The cosmetic may also be in stick form.

The cosmetic may further include a colorant.

Another aspect of the present invention relates to a cosmetic process for caring for and/or making-up keratinic materials, comprising the application onto keratinic materials, in particular onto skin or lips, of the cosmetic.

The oily solid cosmetic of the invention comprises a plant-based and/or an animal-based wax and is excellent in terms of melting sensation, smooth gliding, and also specifically with high-temperature stability and durability.

DETAILED DESCRIPTION OF THE INVENTION

Preferred embodiments of the invention will now be described in detail. However, the present invention is not limited to the embodiments described below.

The oily solid cosmetic of the one of the embodiment comprises (A) candelilla wax, (B) a plant-based and/or animal-based wax with a melting point of 70° C. or higher, (C) a monoester of a monovalent straight-chain saturated fatty acid and a monohydric straight-chain saturated aliphatic alcohol, having a total of 40 to 48 carbon atoms, and (D) at least one selected from the group consisting of (polyglyceryl-2 isostearate/dimer di linoleate) copolymer, hydrogenated castor oil dimer di linoleate, hydrogenated castor oil isostearate, phytosteryl/octyldodecyl lauroyl glutamate, octyldodecyl stearoyl stearate, polyglyceryl-10 isostearate, polyglyceryl-10 diisostearate, polyglyceryl-10 decaisostearate, and polybutene.

The oily solid cosmetic of another embodiment comprises (A) candelilla wax, (B) a plant-based and/or animal-based wax with a melting point of 70° C. or higher, (C) a monoester of a monovalent straight-chain saturated fatty acid and a monohydric straight-chain saturated aliphatic alcohol, having a total of 40 to 48 carbon atoms, and (D) 8 mass % or less of dimer dilinoleyl diisostearate and/or dimer dilinoleyl dimer dilinoleate with respect to the total amount of the oily solid cosmetic.

The "solid" form, as used herein, is the state at ordinary temperature (20° C.). "Solid" generally means a composition having, at a temperature of 20° C. and at atmospheric pressure (760 mmHg), a hardness greater than 30 Nm-1, preferably greater than 40 Nm-1. The hardness can be measured at 20° C. by the so-called "butter-cutting thread" method, which consists in transversely cutting a stick of product, preferably cylindrical of revolution, using a rigid wire 300 μm. by moving the wire relative to the stick at a speed of 60 mm/min. The hardness of the samples is expressed in g and can be measured using a TEXT Plus texturometer.

Candelilla Wax
Component (A)

The oily solid cosmetic of the embodiment comprises candelilla wax as component (A). Candelilla wax is a wax harvested from candelilla grass of the family Euphorbiaceae (*Euphorbia cerifera*). The candelilla wax may be one that is further purified from a partially purified product obtained by removing the extraneous substances from wax extracted from sun-dried candelilla grass by a melting out method.

Purifying treatment of the partially purified product may be carried out, for example, by removal of the resin portion, decoloration or deodorization, or a combination of these. Component (A) is preferably "Candelilla Wax" as listed in the Japan Quasi Drug Raw Material Standards 2006, for example.

The content of component (A) in the oily solid cosmetic of the embodiment may be 2 mass % or more, 3 mass % or more, 4 mass % or more, and may be 12 mass % or less, 10 mass % or less, 9 mass % or less, 8.5 mass % or less, 8 mass % or less, 7 mass % or less, 6 mass % or less, or 5.5 mass % or less, with respect to the total amount of the oily solid cosmetic. The content of component (A) in the oily solid cosmetic of the embodiment may range from 2 to 12 mass %, for example, and is preferably 3 to 10 mass %, 3 to 9 mass % or 4 to 8.5 mass %, with respect to the total amount of the oily solid cosmetic. The "mass %" may also be referred to hereunder as "% by weight".

If the content of component (A) is within these ranges, it is preferred as it will be easier to obtain excellence in terms of melting sensation and smooth gliding.

The mass ratio of component (A) and component (C) (described below) in the oily solid cosmetic of the embodiment may range from 1 to 4:1, for example, and ranges preferably from 1.5 to 3.5:1 and more preferably from 2 to 3:1.

Plant-Based and/or Animal-Based Wax with a Melting Point of 70° C. or Higher
Component (B)

The oily solid cosmetic of the embodiment comprises a plant-based and/or animal-based wax with a melting point of 70° C. or higher as component (B), in addition to the component (A). It is preferable that the oily solid cosmetic comprises a plant-based wax. Component (B) is a substance other than candelilla wax. A plant-based wax and an animal-based wax may be a wax synthesized using a plant-derived and/or an animal-derived material.

The melting point of the wax of component (B) may be 100° C. or below, for example, or 90° C. or below. The melting point of the wax is measured by Melting Point Measuring Method II, which is the general test method according to the Japan Quasi Drug Raw Material Standards.

The wax of component (B) may be carnauba wax, rice bran wax, sunflower seed wax or palm wax, for example.

The oily solid cosmetic of the embodiment preferably comprises at least one selected from the group consisting of carnauba wax, rice bran wax and sunflower seed wax, and more preferably rice bran wax, as component (B). The wax of component (B) may be used as a single type alone, or two or more types may be used in combination.

The wax content of component (B) in the oily solid cosmetic of the embodiment may be 2 mass % or more, 2.5 mass % or more, 3 mass % or more, or 4 mass % or more, and may be 20 mass % or less, 15 mass % or less, 10 mass % or less, 8 mass % or less, 6 mass % or less, 4 mass % or less, or 3 mass % or less, with respect to the total amount of the oily solid cosmetic. The wax content of component (B) in the oily solid cosmetic of the embodiment may range from 2 to 20 mass %, preferably from 3 to 15 mass %, from 3 to 12 mass % or from 3 to 10 mass %, and more preferably from 4 to 8 mass %, with respect to the total amount of the oily solid cosmetic.

The mass ratio of component (B) and component (C) (described below) in the oily solid cosmetic of the embodiment may range from 1 to 6:1, for example, and ranges preferably from 1 to 5:1 and more preferably from 1 to 4:1. The mass ratio of component (B) and component (C) in the oily solid cosmetic of the embodiment may also range from 1.5 to 5:1, in particular from 1.5 to 4:1, or 2 to 4:1. If the mass ratio of component (B) and component (C) is within these ranges it is preferred because the effect of the invention will be superior, and in particular the high-temperature stability will be higher.

The oily solid cosmetic of the embodiment may further comprise a wax other than component (B) and component (A). Although the oily solid cosmetic of the embodiment may comprise a petroleum-derived hydrocarbon wax or synthetic wax as a wax other than component (A) and component (B), it preferably does not comprise a petroleum-derived hydrocarbon wax or synthetic wax. The waxes in the oily solid cosmetic of the embodiment are preferably all naturally-derived.

The total amount of component (A) and component (B) may be 5 mass % or more, 7 mass % or more, 8 mass % or more, 9 mass % or more, or 10 mass % or more, and may be 30 mass % or less, 25 mass % or less, 23 mass % or less, 21 mass % or less, 19 mass % or less, 16 mass % or less, 15 mass % or less, 12 mass % or less, 10 mass % or less, or 8 mass % or less, with respect to the total amount of the oily solid cosmetic. The total amount of component (A) and component (B) may range from 5 to 30 mass %, from 8 to 25 mass %, from 9 to 23 mass %, from 10 to 21 mass %, from 10 to 19 mass % or from 10 to 16 mass %, with respect to the total amount of the oily solid cosmetic. If the total amount of component (A) and component (B) is within these ranges, it is preferred because the melting sensation, smooth gliding, high-temperature stability and durability will be further improved.

When the oily solid cosmetic comprises a wax in addition to component (A) and component (B), the total amount of all of the waxes may be 5 mass % or more, 8 mass % or more, 9 mass % or more, or 10 mass % or more, and 30 mass % or less, 25 mass % or less, 23 mass % or less, 21 mass % or less, 19 mass % or less, or 16 mass % or less, with respect to the total amount of the oily solid cosmetic. The total amount of all of the waxes may range from 5 to 30 mass % or from 8 to 25 mass %, for example, preferably from 9 to 23 mass %, from 10 to 21 mass %, from 10 to 19 mass % or from 10 to 16 mass %, and more preferably from 12 to 13.7%, with respect to the total amount of the oily solid cosmetic of the embodiment. If the total amount of all of the waxes is within these ranges, it is preferred because the melting sensation, smooth gliding, high-temperature stability and durability will be further improved.

Monoester of a Monovalent Fatty Acid and a Monohydric Alcohol

Component (C)

The oily solid cosmetic of the embodiment comprises a monoester of a monovalent straight-chain saturated fatty acid and a monohydric straight-chain saturated aliphatic alcohol, as component (C). The monoester has a total of 40 to 48 carbon atoms. The monoester can be obtained by esterification between a monovalent straight-chain saturated fatty acid and a monohydric straight-chain saturated aliphatic alcohol. The monovalent straight-chain saturated fatty acid and monohydric straight-chain saturated aliphatic alcohol, as the starting materials for the monoester of component (C), are not particularly restricted so long as a monoester with a total of 40 to 48 carbon atoms can be obtained by esterification.

The monovalent fatty acid may be, for example, caprylic acid (octanoic acid), pelargonic acid (nonanoic acid), capric acid (decanoic acid), lauric acid (dodecanoic acid), myristic acid (tetradecanoic acid), pentadecylic acid (pentadecanoic acid), palmitic acid (hexadecanoic acid), margaric acid (heptadecanoic acid), stearic acid (octadecanoic acid), arachidic acid (eicosanoic acid), behenic acid (docosanoic acid), lignoceric acid (tetracosanoic acid), hexacosanoic acid, octacosanoic acid or triacontanoic acid. The monohydric alcohol may be, for example, decanol, undecanol, dodecanol, tridecanol, tetradecanol, pentadecanol, hexadecanol, heptadecanol, stearyl alcohol (octadecanol), nonadecyl alcohol (nonadecanol), arachidyl alcohol (eicosanyl alcohol), henicosyl alcohol, heneicosyl alcohol, behenyl alcohol (docosanyl alcohol), tricosanyl alcohol, lignoceryl alcohol (tetracosanyl alcohol), pentacosanyl alcohol, hexacosanyl alcohol, heptacosanyl alcohol, octacosanyl alcohol, nonacosanyl alcohol, triacontanyl alcohol, hentriacontanyl alcohol or dotriacontanyl alcohol.

The monoester of component (C) is a monoester of a monovalent straight-chain saturated fatty acid and a monohydric straight-chain saturated aliphatic alcohol, and preferably it is a monoester of a monovalent straight-chain saturated fatty acid of 18 to 22 carbon atoms and a monohydric straight-chain saturated aliphatic alcohol of 18 to 22 carbon atoms, because it will be easier to achieve higher crystallinity and higher melting point. The monoester of a monovalent straight-chain saturated fatty acid of 18 to 22 carbon atoms and a monohydric straight-chain saturated aliphatic alcohol of 18 to 22 carbon atoms may be, specifically, behenyl stearate, arachidyl eicosanoate, henicosyl eicosanoate, behenyl eicosanoate, stearyl behenate, nonadecanyl behenate, arachidyl behenate, henicosyl behenate or behenyl behenate.

The monoester of component (C) may be a chemically synthesized product, or it may be one in an oil harvested from a natural source such as a plant or microorganism, or a modified form thereof. The monoester can be synthesized by esterification of a monovalent straight-chain saturated fatty acid and a monohydric straight-chain saturated aliphatic alcohol by a conventionally known method. For example, the monovalent straight-chain saturated fatty acid and monohydric straight-chain saturated aliphatic alcohol are placed in a reactor at a molar ratio of 1:1, and heated under an inert gas atmosphere at 160 to 250° C. for reaction while removing the generated water. A catalyst may either be used or not used during this time. After the reaction, the unreacted fatty acid and alcohol are removed if necessary, from the resulting reaction product. When a catalyst has been used, the catalyst is also removed. If necessary, the reaction product is subjected to purification such as decoloration or deodorization, to obtain the monoester.

The monovalent straight-chain saturated fatty acid and monohydric straight-chain saturated aliphatic alcohol forming the monoester of component (C) may be a chemically synthesized product, or it may be purified from an oil harvested from a natural source such as a plant or microorganism. The monovalent straight-chain saturated fatty acid and monohydric straight-chain saturated aliphatic alcohol forming the monoester are preferably plant-derived 1.0 components.

The ingredient containing the monoester of component (C) is preferably one with a sufficiently high content of the monoester. For the ingredient containing the monoester, the percentage of the monoester content (mass) with respect to the total mass of the ingredient may range from 90 mass % to 100 mass %, for example, preferably from 94 mass % to 100 mass %, and more preferably from 96 mass % to 100 mass %.

An example of a commercial product that may be used as the monoester of component (C) is Unister M-2222SL (NOF Corporation) or Kester Wax K-72 (Koster Keunen).

The content of component (C) in the oily solid cosmetic according to the embodiment may be 1 mass % or more, 1.3 mass % or more, 1.5 mass % or more, or 2 mass % or more, and may be 5 mass % or less, 4 mass % or less, 3.5 mass % or less, or 3 mass % or less, with respect to the total amount of the oily solid cosmetic. The content of component (C) in the oily solid cosmetic according to the embodiment may range from 1 to 5 mass %, preferably from 1.3 to 4 mass %, and more preferably from 1.5 to 3.5 mass % or from 2 to 3 mass %, with respect to the total amount of the oily solid cosmetic.

The content of the monoester of component (C) in the oily solid cosmetic can be analyzed by a conventionally known method, such as an analysis method using gas chromatography. For example, in an analysis method using gas chromatography, the ingredient containing the monoester is used as a measuring sample, and the measuring sample is subjected to gas chromatographic analysis under the following analysis conditions. The sum of the peak areas appearing during the retention time corresponding to the main peaks for a standard substance with a total of 40 carbon atoms and a standard substance with a total of 48 carbon atoms, divided by the total peak area, is the ratio of the content of the monoester with a total of 40 to 48 carbon atoms with respect to the total mass of the measuring sample.

Gas Chromatography Conditions:

Column: DB-1 ht (Agilent Technologies)

Detector: Flame ionization detector (FID),

Temperature-elevating rate: 15° C./min

Column temperature: 50 to 350° C.

Standard substances: monoester with a total of 40 carbon atoms (for example, stearyl behenate), monoester with a total of 48 carbon atoms (for example, tetracosanyl tetracosanoate)

The stearyl behenate and tetracosanyl tetracosanoate used as standard substances can be obtained, for example, by heating behenic acid and stearyl alcohol, or lignoceric acid and lignoceryl alcohol, at a molar ratio of 1:1, under a nitrogen atmosphere, thereby reacting them while removing the generated water. The monovalent fatty acid and monohydric alcohol used for preparation of the standard substances may be ones that are commercially available as reagents (for example, products of Tokyo Chemical Industry Co., Ltd.).

Component (C) may be used as a single type alone, or two or more types may be used in combination. The monoester of component (C) preferably comprises one or more monoesters of a monovalent straight-chain saturated fatty acid of 18 to 22 carbon atoms and a monohydric straight-chain saturated aliphatic alcohol of 18 to 22 carbon atoms, more preferably it comprises one or more selected from the group consisting of stearyl behenate, nonadecanyl behenate, arachidyl behenate, henicosyl behenate, and behenyl behenate, even more preferably it comprises one or more selected from the group consisting of behenyl behenate, and stearyl behenate, and yet more preferably it comprises behenyl behenate.

The oily solid cosmetic of the embodiment may further comprise a monoester other than component (C).

(Component D)

The oily solid cosmetic of the embodiment comprises at least one selected from the group consisting of (polyglyceryl-2 isostearate/dimer dilinoleate) copolymer, hydrogenated castor oil dimer dilinoleate, hydrogenated castor oil isostearate, phytosteryl/octyldodecyl lauroyl glutamate, octyldodecyl stearoyl stearate, polyglyceryl-10 isostearate, polyglyceryl-10 diisostearate, polyglyceryl-10 decaisostearate, polybutene, as component (D).

The content of component (D) in the oily solid cosmetic of the embodiment may be 3 mass % or more, 4 mass % or more, 6 mass % or more, or 8 mass % or more, 10 mass % or more, 15 mass % or more, 20 mass % or more, 30 mass % or more, 40 mass % or more, 50 mass % or more, 55 mass % or more, 60 mass % or more, 65 mass % or more, 70 mass % or more, 75 mass % or more, or 80 mass % or more, with respect to the total amount of the oily solid cosmetic. The content of component (D) in the oily solid cosmetic of the embodiment may be 90 mass % or less, 85 mass % or less, 80 mass % or less, 75 mass % or less, 70 mass % or less, 65 mass % or less, 60 mass % or less, 50 mass % or less, 40 mass % or less, 30 mass % or less, 25 mass % or less, 20 mass % or less, 17 mass % or less, 15 mass % or less, or 13 mass % or less, with respect to the total amount of the oily solid cosmetic. The content of component (D) in the oily solid cosmetic of the embodiment may range from 3 to 90 mass %. In a particular embodiment, the content of component (D) in the oily solid cosmetic of the embodiment may range from 3 to 20 mass %, in particular from 4 to 17 mass % with respect to the total amount of the oily solid cosmetic. In another particular and preferred embodiment, the content of component (D) may range from 20 to 70 mass %, from 22 to 60 mass %, preferably from 24 to 50 mass %, and more preferably from 25 to 45 mass %, with respect to the total amount of the oily solid cosmetic. If the content of component (D) is within these ranges, the effect of the invention will be superior and it will be possible to obtain an oily solid cosmetic with particularly excellent durability.

The oily solid cosmetic of the embodiment may comprise dimer dilinoleyl diisostearate and/or dimer dilinoleyl dimer dilinoleate as the component (D). When the cosmetic comprises dimer dilinoleyl diisostearate and/or dimer dilinoleyl dimer dilinoleate as the component (D), the total content of dimer dilinoleyl diisostearate and dimer dilinoleyl dimer dilinoleate is 8 mass % or less, and may be 7 mass % or less, 6 mass % or less, or 5 mass % or less, with respect to the total amount of the oily solid cosmetic. The total content of dimer dilinoleyl diisostearate and dimer dilinoleyl dimer dilinoleate may be 3 mass % or more, or 4 mass % or more, with respect to the total amount of the oily solid cosmetic. In a particular embodiment, the total content of dimer dilinoleyl diisostearate and dimer dilinoleyl dimer dilinoleate ranges from 3 mass % to 8 mass % in particular from 4 mass % to 7 mass % with respect to the total amount of the oily solid cosmetic.

Component (D) may be a naturally-derived such as plant-derived. As component (D) of which the fatty acid and the alcohol as the starting materials are plant-derived, HAILU-CENT ISDA (Kokyu Alcohol Kogyo Co., LTD.) may be used.

Oils

The oily solid cosmetic of the embodiment preferably further comprises an oil as component (E), in addition to component (A), (B), (C) and (D). Component (E) is not particularly restricted and may be a polar oil or non-polar oil, and in semi-solid or liquid form, for example. Component (E) may be naturally-derived, such as plant-derived or animal-derived, or it may be petroleum-derived. In particular embodiment, component (E) is an oil having at least one hydroxyl group. Component (E) may be used as a single type alone, or two or more types may be used in combination.

Examples of component (E) include polyglyceryl-2 triisostearate, polyglyceryl-2 tetraisostearate, hydrogenated-2 castor oil dimer dilinoleate and caprylic/capric triglyceride, squalane, phytosteryl/octyldodecyl lauroyl glutamate, polyglyceryl-2 diisostearate, jojoba seed oil, jojoba ester, octyldodecyl myristate, isostearyl isostearate, isostearyl alcohol, octyldodecanol, diisostearyl malate, polyglyceryl-10 nonaisostearate, sunflower seed oil, pentaerythrityl tetraisostearate, and tridecyl trimellitate.

Component (E) preferably comprises a liquid oil having at least one hydroxyl group. Examples of liquid oils having at least one hydroxyl group include polyglyceryl-2 triisostearate, diisostearyl malate, for example. Furthermore, component (E) preferably comprises squalane and/or phytosteryl/octyldodecyl lauroyl glutamate.

The content of component (E) in the oily solid cosmetic of the embodiment may be 35 mass % or more, 37 mass % or more, 38 mass % or more, 40 mass % or more, 45 mass % or more, 50 mass % or more, 55 mass % or more, 60 mass % or more, 65 mass % or more, 70 mass % or more, 75 mass % or more, or 80 mass % or more, with respect to the total amount of the oily solid cosmetic. The content of component (E) in the oily solid cosmetic of the embodiment may be 90 mass % or less, 88 mass % or less, 85 mass % or less, 82 mass % or less, 80 mass % or less, 75 mass % or less, 70 mass % or less, 65 mass % or less, 60 mass % or less, 55 mass % or less, or 50 mass % or less, with respect to the total amount of the oily solid cosmetic. The content of component (E) in the oily solid cosmetic of the embodiment may range from 35 to 85 mass %, from 37 to 82 mass %, from 38 to 80 mass %, from 38 to 70 mass %, from 38 to 60 mass % or from 38 to 50 mass %, with respect to the total amount of the oily solid cosmetic.

The mass ratio of component (E) and component (D) in the oily solid cosmetic of the embodiment may range from 1 to 16:1, from 2 to 16:1, from 3 to 16:1, from 4 to 16:1, from 6 to 16:1, from 1 to 14:1, from 1 to 12:1, from 1 to 10:1, from 1 to 9:1, from 1 to 7:1, from 1 to 6:1, 1: from 1 to 16, 1: from 2 to 16, 1: from 3 to 16, 1: from 4 to 16, 1: from 6 to 16, 1: from 1 to 14, 1: from 1 to 12, 1: from 1 to 10, 1: from 1 to 9, 1: from 1 to 7, 1: from 1 to 6. The mass ratio of component (E) and component (D) in the oily solid cosmetic of the embodiment ranges preferably from 6 to 13:1, from 6 to 11:1 or from 6 to 9:1.

Colorants

The oily solid cosmetic of the embodiment may also comprise a colorant. The colorant may be an organic synthetic dye, a natural dye, an inorganic pigment or a glossy pigment, for example. An organic synthetic dye may be a dye, lake or organic pigment, for example, and an inorganic pigment may be an extender pigment, color pigment or white pigment, for example. The oily solid cosmetic of the embodiment does not need to comprise a colorant. An oily solid cosmetic without a colorant is suitable as a lip cream, for example. When the oily solid cosmetic of the embodiment comprises a colorant, the colorant content may range from 0.01 to 30 mass % or from 0.001 to 2 mass %, for example, with respect to the total amount of the oily solid cosmetic.

The oily solid cosmetic of the embodiment may also comprise water. However, the oily solid cosmetic according to the embodiment preferably includes substantially no water. The water content of the oily solid cosmetic may be no greater than 1.0 mass %, preferably no greater than 0.5 mass %, more preferably no greater than 0.3 mass % and even more preferably no greater than 0.1 mass %, with respect to the total amount of the oily solid cosmetic.

The oily solid cosmetic of the embodiment may also comprise other components. Examples of such other components that may be used are antioxidants, preservatives, ultraviolet absorbers, humectants, surfactants, solvents, aromatics, chemical agents, chelating agent, and pH adjuster.

The oily solid cosmetic of the embodiment may be a cosmetic for makeup that is to be applied onto skin or lips, for example. The oily solid cosmetic may be a lip rouge, a cheek rouge, a lip balm, a lip liner, a foundation, a concealer, a face color, an eyeliner, or an eye shadow, for example. In a particular embodiment, the oily solid cosmetic is a lip rouge, a lip balm, or a lip liner. The natural origin index (without water) as defined in ISO 16128 of the oily solid cosmetic according to the embodiment may be 80% or higher, preferably 85% or higher, more preferably 90% or higher, further preferably 95% or higher. The natural origin index also may be 98% or higher. The natural origin index may be less than 100%, and preferably 99% or less.

The oily solid cosmetic of the embodiment may be in the form of a stick, for example, or in any other desired form. The oily solid cosmetic of the embodiment may be housed in a container, such as a stick-shaped container or a thin dish-shaped container, for example. The oily solid cosmetic of the embodiment is preferably not a powder-packed solid. Because the oily solid cosmetic according to the embodiment has sufficiently high durability, it is particularly suitable for use as a stick-shaped cosmetic.

The oily solid cosmetic of the embodiment can be produced by a common method, and for example, it can be produced by heating and dissolving each of the starting materials as necessary, mixing them to uniformity, and cooling the mixture to be solidified.

Another aspect of the embodiment relates to a cosmetic process for caring for and/or making-up keratinic materials, comprising the application onto keratinic materials, in particular onto skin or lips, of the oily solid cosmetic of the invention.

Examples

The invention will now be illustrated by examples, with the understanding that the invention is not meant to be limited to these examples.

Lipsticks having the compositions listed in Tables 1, 3 and 5 were prepared. The compositions comprise ingredients expressed in % by weight of total weight of the composition. Each lipstick was obtained according to a common method, heating and melting a wax, mixing all of the components and molding the mixture using a stick-shaped container. Tables 2, 4 and 6 show the mass ratio of component (A) with respect to component (C), the mass ratio of component (B) with respect to component (C), the mass ratio of component (E) with respect to component (D), and the total amount of the wax, for each oily solid cosmetic.

The details of the components used in each Example are as follows.

Candelilla (*Euphorbia cerifera*) Wax: INA Trading, Candelilla wax SR-3

Rice (*Oryza sativa*) Bran Wax: Cerarica Noda, Rice Wax N° 1

Carnauba (*Copernicia cerifera*) Wax: Baerlocher FR, Cerauba Jaune Flor Paillettes Sunflower (*Helianthus annuus*) seed wax: Yokozeki Oil & Fat Industries Co., Ltd. Polyglyceryl-2 Isostearate/Dimer Dilinoleate Copolymer: Kokyu Alcohol Kogyo Co., Ltd., HAILUCENT ISDA Hydrogenated Castor Oil Dimer Dilinoleate: Kokyu Alcohol Kogyo Co., Ltd., RISOCAST DA-L Dimer Dilinoleyl Diisostearate: NIPPON FINE CHEMICAL CO., LTD., LUSPLAN DD-DA7

Hydrogenated Castor Oil Isostearate: KOKYU ALCOHOL KOGYO, RISOCAST MIS

Phytosteryl/Octyldodecyl Lauroyl Glutamate: Ajinomoto Co., Inc., ELDEW PS-203

Octyldodecyl Stearoyl Stearate: KOKYU ALCOHOL KOGYO, RISOCAST ODSHS

Polyglyceryl-10 Isostearate: SAKAMOTO YAKUHIN KOGYO, S FACE IS-1001P

Polyglyceryl-10 Diisostearate: SAKAMOTO YAKUHIN KOGYO, S FACE IS-1002P

Polyglyceryl-10 Decaisostearate: SAKAMOTO YAKUHIN KOGYO, S FACE IS-1009P

Polyglyceryl-2 Tetraisostearate: SAKAMOTO YAKUHIN KOGYO, S FACE IS-204P

TABLE 1

|   |   | Examples | | | | | | | | | |
|---|---|---|---|---|---|---|---|---|---|---|---|
|   |   | 1 | 2 | 3 | 4 | 5 | 6 | 7 | 8 | 9 | 10 |
| A | Candelilla Wax | 7.00 | 3.30 | 8.20 | 7.00 | 7.00 | 7.00 | 7.00 | 5.50 | 5.50 | 5.50 |
| B | Rice Bran Wax | 7.00 | 5.30 | 8.20 | — | — | 7.00 | 7.00 | 5.50 | 5.50 | 5.50 |
|   | Carnauba Wax | — | — | — | 7.00 | — | — | — | — | — | — |
|   | Sunflower Seed Wax | — | — | — | — | 7.00 | — | — | — | — | — |
| C | Behenyl Behenate | 3.00 | 1.40 | 3.50 | 3.00 | 3.00 | 3.00 | 3.00 | 2.50 | 2.50 | 2.50 |
|   | Stearyl Stearate | — | — | — | — | — | — | — | — | — | — |
| D | Polyglyceryl-2 Isostearate/Dimer Dilinoleate Copolymer | 10.00 | 10.00 | 10.00 | 10.00 | 10.00 | 5.00 | 15.00 | 10.00 | 10.00 | 10.00 |
|   | Hydrogenated Castor Oil Dimer Dilinoleate | — | — | — | — | — | — | — | 6.00 | 6.00 | 6.00 |
|   | Phytosteryl/Octyldodecyl Lauroyl Glutamate | — | — | — | — | — | — | — | — | — | 8.00 |
| E | Polyglyceryl-2 Triisostearate | 72.80 | 79.80 | 69.90 | 72.80 | 72.80 | 77.80 | 67.80 | 30.30 | 55.30 | 47.30 |
|   | Caprylic/Capric Triglyceride | — | — | — | — | — | — | — | 40.00 | — | — |
|   | Squalane | — | — | — | — | — | — | — | — | 15.00 | 15.00 |
|   | Red 7 | 0.20 | 0.20 | 0.20 | 0.20 | 0.20 | 0.20 | 0.20 | 0.20 | 0.20 | 0.20 |
| Total | | 100.0 | 100.0 | 100.0 | 100.0 | 100.0 | 100.0 | 100.0 | 100.0 | 100.0 | 100.0 |

TABLE 2

|   | Examples | | | | | | | | | |
|---|---|---|---|---|---|---|---|---|---|---|
|   | 1 | 2 | 3 | 4 | 5 | 6 | 7 | 8 | 9 | 10 |
| Ratio of A/C | 2.33 | 2.36 | 2.34 | 2.33 | 2.33 | 2.33 | 2.33 | 2.20 | 2.20 | 2.20 |
| Ratio of B/C | 2.33 | 3.79 | 2.34 | 2.33 | 2.33 | 2.33 | 2.33 | 2.20 | 2.20 | 2.20 |
| Wax Amount (%) | 17.00 | 10.00 | 19.90 | 17.00 | 17.00 | 17.00 | 17.00 | 13.50 | 13.50 | 13.50 |
| Ratio of E/D | 7.28 | 7.98 | 6.99 | 7.28 | 7.28 | 15.56 | 4.52 | 4.39 | 4.39 | 2.60 |

TABLE 3

|   |   | 11 | 12 | 13 | 14 | 15 | 16 | 17 |
|---|---|---|---|---|---|---|---|---|
| A | Candelilla Wax | 7.00 | 7.00 | 7.00 | 7.00 | 7.00 | 7.00 | 7.00 |
| B | Rice Bran Wax | 7.00 | 7.00 | 7.00 | 7.00 | 7.00 | 7.00 | 7.00 |
| C | Behenyl Behenate | 3.00 | 3.00 | 3.00 | 3.00 | 3.00 | 3.00 | 3.00 |
| D | Dimer Dilinoleyl Diisostearate | 5.00 | | | | | | |
|   | Dimer Dilinoleyl Dimer Dilinoleate | | 5.00 | | | | | |
|   | Hydrogenated Castor Oil Dimer Dilinoleate | | | 10.00 | | | | |
|   | Hydrogenated Castor Oil Isostearate | | | | 10.00 | | | |
|   | Phytosteryl/Octyldodecyl Lauroyl Glutamate | | | | | 10.00 | | |
|   | Octyldodecyl Stearoyl Stearate | | | | | | 10.00 | |
|   | Polyglyceryl-10 Isostearate | | | | | | | 10.00 |
| E | Polyglyceryl-2 Triisostearate | 77.80 | 77.80 | 72.80 | 72.80 | 72.80 | 72.80 | 72.80 |
| F | Red 7 | 0.20 | 0.20 | 0.20 | 0.20 | 0.20 | 0.20 | 0.20 |

TABLE 4

| | Examples | | | | | | |
|---|---|---|---|---|---|---|---|
| | 11 | 12 | 13 | 14 | 15 | 16 | 17 |
| Ratio of A/C | 2.33 | 2.33 | 2.33 | 2.33 | 2.33 | 2.33 | 2.33 |
| Ratio of B/C | 2.33 | 2.33 | 2.33 | 2.33 | 2.33 | 2.33 | 2.33 |
| Wax Amount (%) | 17.00 | 17.00 | 17.00 | 17.00 | 17.00 | 17.00 | 17.00 |
| Ratio of E/D | 15.56 | 7.28 | 7.28 | 7.28 | 7.28 | 7.28 | 15.56 |

TABLE 5

| | | 18 | 19 | 20 | 21 | 22 | 23 | 24 | 25 |
|---|---|---|---|---|---|---|---|---|---|
| A | Candelilla Wax | 7.00 | 7.00 | 7.00 | 5.00 | 3.00 | 5.00 | 3.00 | 5.00 |
| B | Rice Bran Wax | 7.00 | 7.00 | 7.00 | 1.00 | 1.50 | — | — | — |
| | Carnauba Wax | — | — | — | — | 2.00 | 2.00 | — | — |
| | Sunflower Seed Wax | — | — | — | 1.50 | 2.50 | 3.00 | 3.00 | 3.00 |
| C | Behenyl Behenate | 3.00 | 3.00 | 3.00 | 2.50 | 3.00 | 1.40 | 1.50 | 3.00 |
| D | Polyglyceryl-2 Isostearate/Dimer Dilinoleate Copolymer | — | — | — | 5.00 | — | — | 10.00 | — |
| | Dimer Dilinoleyl Diisostearate | — | — | — | — | 3.00 | — | 3.00 | 2.00 |
| | Dimer Dilinoleyl Dimer Dilinoleate | — | — | — | — | — | 4.00 | — | 2.00 |
| | Hydrogenated Castor Oil Dimer Dilinoleate | | | | 10.00 | | | 20.00 | 13.00 |
| | Hydrogenated Castor Oil Isostearate | | | | | 10.00 | | | |
| | Phytosteryl/Octyldodecyl Lauroyl Glutamate | | | | 5.00 | | | 13.00 | |
| | Octyldodecyl Stearoyl Stearate | | | | | | 10.00 | | 15.00 |
| | Polyglyceryl-10 Isostearate | | | | | | 4.00 | | |
| | Polyglyceryl-10 Diisostearate | 10.00 | | | | | | | |
| | Polyglyceryl-10 Decaisostearate | | 10.00 | | | 20.00 | | | |
| | Polybutene | | | 10.00 | | | 10.00 | | |
| E | Polyglyceryl-2 Triisostearate | 72.80 | 72.80 | 72.80 | 29.80 | 30.80 | 35.40 | 31.30 | 27.80 |
| | Polyglyceryl-2 Tetraisostearate | | | | | | | | 15.00 |
| | Caprylic/Capric Triglyceride | | | | | 10.00 | | | 5.00 |
| | Squalane | | | | 10.00 | | | 10.00 | |
| | Helianthus Annuus (Sunflower) Seed Oil | | | | 10.00 | | 10.00 | | |
| | Jojoba Esters | | | | 10.00 | | | 3.00 | |
| | Diisostearyl Malate | | | | 5.00 | | 5.00 | | |
| | Pentaerythrityl Tetraisostearate | | | | | 4.00 | | | 7.00 |
| | Octyldodecanol | | | | | 10.00 | 10.00 | | |
| | Tridecyl Trimellitate | | | | 5.00 | | | 2.00 | 2.00 |
| F | Red 7 | 0.20 | 0.20 | 0.20 | 0.20 | 0.20 | 0.20 | 0.20 | 0.20 |

TABLE 6

| | Examples | | | | | | | |
|---|---|---|---|---|---|---|---|---|
| | 18 | 19 | 20 | 21 | 22 | 23 | 24 | 25 |
| Ratio of A/C | 2.33 | 2.33 | 2.33 | 2.00 | 1.00 | 3.57 | 2.00 | 1.67 |
| Ratio of B/C | 2.33 | 2.33 | 2.33 | 1.00 | 2.00 | 3.57 | 2.00 | 1.00 |

TABLE 6-continued

| | Examples | | | | | | | |
|---|---|---|---|---|---|---|---|---|
| | 18 | 19 | 20 | 21 | 22 | 23 | 24 | 25 |
| Wax Amount (%) | 17.00 | 17.00 | 17.00 | 10.00 | 12.00 | 11.40 | 7.50 | 11.00 |
| Ratio of E/D | 7.28 | 7.28 | 7.28 | 3.49 | 1.66 | 2.16 | 1.01 | 1.78 |

TABLE 7

| | | Comparative Examples | | | | | | |
|---|---|---|---|---|---|---|---|---|
| | | 1 | 2 | 3 | 4 | 5 | 6 | 7 |
| A | Candelilla Wax | — | 7.00 | 7.00 | 7.00 | 7.00 | 7.00 | 7.00 |
| B | Rice Bran Wax | 7.00 | — | 7.00 | 7.00 | 7.00 | 7.00 | 7.00 |
| | Carnauba Wax | — | — | — | — | — | — | — |
| | Sunflower Seed Wax | — | — | — | — | — | — | — |
| C | Behenyl Behenate | 3.00 | 3.00 | — | 3.00 | — | 3.00 | 3.00 |
| | Stearyl Stearate | | | | | 3.00 | — | — |
| D | Polyglyceryl-2 Isostearate/Dimer Dilinoleate Copolymer | 10.00 | 10.00 | 10.00 | — | 10.00 | | |
| | Dimer Dilinoleyl Diisostearate | | | | | — | 10.00 | — |
| | Dimer Dilinoleyl Dimer Dilinoleate | | | | | — | — | 10.00 |
| E | Polyglyceryl-2 Triisostearate | 79.80 | 79.80 | 75.80 | 82.80 | 72.80 | 72.80 | 72.80 |
| | Hydrogenated Castor Oil | — | — | — | — | — | — | — |
| | Dimer Dilinoleate | | | | | | | |
| | Caprylic/Capric Triglyceride | — | — | — | — | — | — | — |
| | Squalane | — | — | — | — | — | — | — |
| | Phytosteryl/Octyldodecyl Lauroyl Glutamate | — | — | — | — | — | — | — |
| | Red 7 | 0.20 | 0.20 | 0.20 | 0.20 | 0.20 | 0.20 | 0.20 |
| Total | | 100.0 | 100.0 | 100.0 | 100.0 | 100.0 | 100.0 | 100.0 |

TABLE 8

| | Comparative Examples | | | | | | |
|---|---|---|---|---|---|---|---|
| | 1 | 2 | 3 | 4 | 5 | 6 | 7 |
| Ratio of A/C | 0.00 | 2.33 | — | 2.33 | 2.33 | 2.33 | 2.33 |
| Ratio of B/C | 2.33 | 0.00 | — | 2.33 | 2.33 | 2.33 | 2.33 |
| Wax Amount (%) | 10.00 | 10.00 | 14.00 | 17.00 | 14.00 | 17.00 | 17.00 |
| Ratio of E/D | 7.98 | 7.98 | 7.58 | — | 7.28 | 7.28 | 7.28 |

[Organoleptic Evaluation]

An organoleptic evaluation was conducted for the oily solid cosmetics of the Examples and Comparative Examples. The organoleptic evaluation was conducted by molding the oily solid cosmetic into a stick form and coating the stick onto lips. The parameters for the organoleptic evaluation were melting sensation, smooth gliding texture and color payoff. The melting sensation is the sensation of melting when placed on the lips. The smooth gliding texture is the sensation of smooth spreading without sticking. The color payoff is the satisfaction of coloration of the coated film (makeup film).

The organoleptic evaluation was based on a single use on the lips by an evaluation panel of 10 cosmetic experts (25 to 55 years of age), with evaluation on the following scale. Overall excellence was considered to be an evaluation of 'A' to 'C'. The results are shown in Tables 9 to 12.
A: Excellent
B: Better
C: Good
D: Not passable
E: Not good
F: Bad
[Quality and Stability Evaluation]

The quality and stability of the oily solid cosmetics of the Examples and Comparative Examples were evaluated. For quality, the oily solid cosmetic was molded into the form of a stick and allowed to stand at 25° C. for 24 hours, after which the oily solid cosmetic was let out from the container to a length of 5 mm and coated with 10 passes onto the palm of the hand, during which time the condition of the cosmetic was evaluated by observation. Based on the results of evaluating the condition of the cosmetic that had been coated with 10 passes, an evaluation of "F" was assigned when the form of the stick was not lost. An evaluation of "A" was assigned when it could be used without any problem.

For stability, the oily solid cosmetic that had been molded into a stick form was allowed to stand at 45° C. for 1 month with the top of the stick pointing upward, and evaluation was conducted based on observation of the outer appearance. Based on the results of evaluating the outer appearance, an evaluation of "F" was assigned when a significant change (blooming) was produced or the stick form could not be maintained. An evaluation of "A" was assigned when no change in outer appearance was observed. When the evaluation result was "A" for both evaluations of the quality and stability, it was judged to have excellent quality and stability. The results are shown in Tables 9 to 12.

TABLE 9

| | Examples | | | | | | | | | |
|---|---|---|---|---|---|---|---|---|---|---|
| | 1 | 2 | 3 | 4 | 5 | 6 | 7 | 8 | 9 | 10 |
| Melting sensation | B | A | C | B | B | B | B | A | A | A |
| Smooth gliding texture | B | B | C | B | B | A | C | A | B | A |
| Color payoff | B | A | C | B | B | A | B | A | B | A |
| Break test | A | A | A | A | A | A | A | A | A | A |
| Stability | A | A | A | A | A | A | A | A | A | A |

TABLE 10

| | Examples | | | | | | |
| | 11 | 12 | 13 | 14 | 15 | 16 | 17 |
|---|---|---|---|---|---|---|---|
| Melting sensation | B | B | A | A | B | C | C |
| Smooth gliding texture | C | C | C | C | B | A | C |
| Color payoff | B | B | A | A | B | A | B |
| Break test | A | A | A | A | A | A | A |
| Stability | A | A | A | A | A | A | A |

TABLE 11

| | Examples | | | | | | | |
| | 18 | 19 | 20 | 21 | 22 | 23 | 24 | 25 |
|---|---|---|---|---|---|---|---|---|
| Melting sensation | C | C | C | A | A | A | A | A |
| Smooth gliding texture | C | A | B | A | A | A | A | A |
| Color payoff | B | A | B | A | A | A | A | A |
| Break test | A | A | A | A | A | A | A | A |
| Stability | A | A | A | A | A | A | A | A |

TABLE 12

| | Comparative Examples | | | | | | |
| | 1 | 2 | 3 | 4 | 5 | 6 | 7 |
|---|---|---|---|---|---|---|---|
| Melting sensation | D | B | D | B | B | C | D |
| Smooth gliding texture | B | A | C | B | B | D | E |
| Color payoff | D | B | E | B | B | C | D |
| Break test | F | A | A | F | F | A | A |
| Stability | A | F | F | A | F | F | F |

The results presented in Tables demonstrated that all of the oily solid cosmetics of the examples of the present invention comprising compounds (A) to (D) were excellent both in terms of melting sensation, smooth gliding texture, color payoff, and also specifically in term of break test and stability (note 'A' meaning excellent quality and stability for all compositions), in comparison to comparative examples that are missing one or several of the compounds (A) to (D).

The invention claimed is:

1. An oily solid cosmetic comprising:
(A) candelilla wax,
(B) one or more plant-based wax with a melting point of 70° C. or higher selected from the group consisting of rice bran wax and sunflower seed wax,
(C) behenyl behenate, and
(D) at least one selected from the group consisting of (polyglyceryl-2 isostearate/dimer dilinoleate) copolymer, hydrogenated castor oil dimer dilinoleate, hydrogenated castor oil isostearate, and octyldodecyl stearoyl stearate, and
one or more liquid oil(s) (E) having at least one hydroxyl group, in addition to the component (D), selected from the group consisting of polyglyceryl-2 triisostearate, caprylic/capric triglyceride, squalane, jojoba ester, octyldodecanol, diisostearyl malate, sunflower seed oil, pentaerythrityl tetraisostearate, tridecyl trimellitate, and mixtures thereof,
wherein
the amount of component (A) ranges from 3 to 7 mass %, with respect to the total amount of the oily solid cosmetic,
the total amount of component(s) (B) ranges from 2 to 10 mass %, with respect to the total amount of the oily solid cosmetic,
and
the total amount of component (A) and component (B) ranges from 5 to 16 mass %, with respect to the total amount of the oily solid cosmetic.

2. The cosmetic according to claim 1, wherein the plant-based wax is rice bran wax.

3. The cosmetic according to claim 1, wherein the cosmetic is a lip rouge, a cheek rouge, a lip balm, a lip liner, a foundation, a concealer, a face color, an eyeliner, or an eye shadow.

4. The cosmetic according to claim 1, wherein the cosmetic is in the form of a stick.

5. The cosmetic according to claim 1, further comprising a colorant.

6. A cosmetic process for caring for and/or making-up keratinic materials, comprising the application onto keratinic materials of the cosmetic according to claim 1.

7. The cosmetic according to claim 1, wherein the liquid oil comprises at least polyglyceryl-2 triisostearate.

8. The cosmetic according to claim 1, wherein:
the total amount of component (C) ranges from 1 to 5 mass % with respect to the total amount of the oily solid cosmetic,
the total amount of component (D) ranges from 3 to 30 mass % with respect to the total amount of the oily solid cosmetic, and
the total amount of component (E) ranges from 45 to 85 mass % with respect to the total amount of the oily solid cosmetic.

* * * * *